US008831304B2

(12) United States Patent
Xu et al.

(10) Patent No.: US 8,831,304 B2
(45) Date of Patent: Sep. 9, 2014

(54) BLOOD VESSEL SEGMENTATION WITH THREE-DIMENSIONAL SPECTRAL DOMAIN OPTICAL COHERENCE TOMOGRAPHY

(75) Inventors: Juan Xu, Monroeville, PA (US); David Tolliver, Pittsburgh, PA (US); Hiroshi Ishikawa, Pittsburgh, PA (US); Chaim Gad Wollstein, Pittsburgh, PA (US); Joel S. Schuman, Pittsburgh, PA (US)

(73) Assignees: University of Pittsburgh—Of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 305 days.

(21) Appl. No.: 13/321,301

(22) PCT Filed: May 27, 2010

(86) PCT No.: PCT/US2010/036274
§ 371 (c)(1),
(2), (4) Date: May 3, 2012

(87) PCT Pub. No.: WO2010/138645
PCT Pub. Date: Dec. 2, 2010

(65) Prior Publication Data
US 2012/0213423 A1 Aug. 23, 2012

Related U.S. Application Data

(60) Provisional application No. 61/182,495, filed on May 29, 2009.

(51) Int. Cl.
| | |
|---|---|
| G06K 9/00 | (2006.01) |
| G01B 9/02 | (2006.01) |
| A61B 5/00 | (2006.01) |
| G06K 9/46 | (2006.01) |
| G06T 7/00 | (2006.01) |
| G06T 19/00 | (2011.01) |
| G01N 21/47 | (2006.01) |
| A61B 5/02 | (2006.01) |

(52) U.S. Cl.
CPC ............ *G06T 19/00* (2013.01); *G01B 9/02044* (2013.01); *A61B 5/0073* (2013.01); *G06K 9/0061* (2013.01); *G06K 9/4609* (2013.01); *G06T 7/0087* (2013.01); *G01B 9/02091* (2013.01); *G06T 2207/30101* (2013.01); *G06T 2207/10101* (2013.01); *G06K 2009/00932* (2013.01); *G01B 9/02083* (2013.01); *G06T 7/0081* (2013.01); *G06T 2210/41* (2013.01); *G01N 21/4795* (2013.01); *A61B 5/02007* (2013.01)
USPC ........................................................ 382/128

(58) Field of Classification Search
None
See application file for complete search history.

(56) References Cited

U.S. PATENT DOCUMENTS

| | | | | |
|---|---|---|---|---|
| 7,474,775 | B2 * | 1/2009 | Abramoff et al. | 382/128 |
| 2006/0119858 | A1 * | 6/2006 | Knighton et al. | 356/479 |

(Continued)

FOREIGN PATENT DOCUMENTS

| | | |
|---|---|---|
| JP | 2008-22928 A | 2/2008 |
| WO | WO-2008/010305 A1 | 1/2008 |

OTHER PUBLICATIONS

International Search Report WO 2010/138645 dated Jan. 14, 2011.

*Primary Examiner* — Hadi Akhavannik
(74) *Attorney, Agent, or Firm* — Foley & Lardner LLP

(57) ABSTRACT

In the context of the early detection and monitoring of eye diseases, such as glaucoma and diabetic retinopathy, the use of optical coherence tomography presents the difficulty, with respect to blood vessel segmentation, of weak visibility of vessel pattern in the OCT fundus image. To address this problem, a boosting learning approach uses three-dimensional (3D) information to effect automated segmentation of retinal blood vessels. The automated blood vessel segmentation technique described herein is based on 3D spectral domain OCT and provides accurate vessel pattern for clinical analysis, for retinal image registration, and for early diagnosis and monitoring of the progression of glaucoma and other retinal diseases. The technique employs a machine learning algorithm to identify blood vessel automatically in 3D OCT image, in a manner that does not rely on retinal layer segmentation.

12 Claims, 7 Drawing Sheets

(56) References Cited

U.S. PATENT DOCUMENTS

| | | | |
|---|---|---|---|
| 2006/0257031 A1* | 11/2006 | Abramoff et al. | 382/224 |
| 2007/0140541 A1 | 6/2007 | Bae et al. | |
| 2007/0285619 A1 | 12/2007 | Aoki et al. | |
| 2008/0068560 A1* | 3/2008 | Knighton et al. | 351/206 |
| 2008/0095411 A1* | 4/2008 | Hwang et al. | 382/117 |
| 2009/0180123 A1* | 7/2009 | Knighton et al. | 356/479 |
| 2010/0033501 A1* | 2/2010 | Whitesell et al. | 345/634 |
| 2010/0208201 A1* | 8/2010 | Knighton et al. | 351/206 |
| 2011/0274338 A1* | 11/2011 | Park et al. | 382/133 |

\* cited by examiner

BLOOD VESSEL SEGMENTATION WITH THREE-DIMENSIONAL SPECTRAL DOMAIN OPTICAL COHERENCE TOMOGRAPHY

STATEMENT REGARDING FEDERALLY SPONSORED RESEARCH

This invention was made with government support under RO1-EY013178-8, awarded by the National Institutes of Health. The United States government has certain rights in this invention.

CROSS-REFERENCE TO RELATED PATENT APPLICATIONS

This application claims priority from U.S. Provisional Application Ser. No. 61/182,495, filed May 29, 2009, which is incorporated herein by reference in its entirety.

BACKGROUND OF THE INVENTION

Spectral domain optical coherence tomography (SD-OCT) is a new high resolution imaging technique, capable of achieving micrometer resolution in depth. It allows detailed imaging of the eye structures. Three-dimensional (3D) OCT, which can yield 3D (cube) images of the retina, is a promising technique for automated analysis, early detection, and monitoring the progression of eye diseases, such as glaucoma, diabetic retinopathy and others.

A blood vessel on a retinal image is not only an indicator of various eye diseases, but also an important feature to register the retinal images of the same patient taken at different visits, or even taken with different ophthalmic devices. This greatly improves accuracy in the monitoring of eye disease progression. Additionally, a blood vessel can be used as a landmark to measure other normal or abnormal features on the retina.

A 3D OCT retinal image is comprised of a series of cross-sectional scans (B-scan, x-z plane in FIG. 1(a)) from top to bottom of the scanning region of the retina. Each B-scan consists of certain number of high-resolution one-dimensional scan in z direction (A-scan). A blood vessel generates a shadow on the outer retinal layers, as shown in FIG. 1(b). When an OCT fundus image is generated (FIG. 1(c)) by averaging each A-scan, the visibility of vessel pattern may decrease due to the noise and high reflection on the top layers of the retina. This makes vessel segmentation on OCT image a challenge, compared to a conventional 2D fundus image.

Niemeijer et al. [1] introduced an automated vessel segmentation algorithm for 3D OCT imaging. Retinal layer segmentation was required to generate a 2D OCT fundus image by taking the 2D projection of certain retinal layers, thereby to enhance vessel pattern. A supervised, pixel-classification approach was applied to 2D projection to detect blood vessel. The authors tested the approach on the samples with well-segmented retinal layers and obtained 0.97 of an area under the ROC curve. This approach is limited in that its performance highly depends on retinal layer segmentation.

Most other retinal vessel segmentation techniques are based on conventional 2D fundus imaging, which can be roughly classified into several major categories: matched filter based method [2,3], thresholding based method [4], tracking based method [5], mathematical morphology method [6], and classification based method [7,8]. The matched filter method entails convolving the image with a directional filter designed according to the vessel profile [3], such as Gaussian [2] and second-order Gaussian filter [3]. Hoover et al. [4] introduced a piecewise thresholding probe algorithm, for matched filter response (MFR) imaging, which yielded a 90% true positive detection rate compared with the hand-labeled blood vessel as the ground truth. Staal et al. [7] described a pixel classification method for color retinal imaging. Feature vectors first were computed for each pixel, and then a k-Nearest neighbor (kNN) classifier was used to classify a given pixel as either vessel or non-vessel.

SUMMARY OF THE INVENTION

It is an object of the present invention to provide a three-dimensional boosting learning algorithm trained to automatically identify and/or segment retinal blood vessels in a 3D OCT image without replying pre-segmentation. This allows the clinicians to obtain accurate pattern of the blood vessels for clinical analysis, for retinal image registration, and for early diagnosis and monitoring of the progression of glaucoma and other retinal diseases.

In contrast to conventional techniques, which use 2D image properties to detect blood vessels, the present invention employs a 3D boosting learning algorithm, which employs both 2D information on OCT fundus image and the third-dimensional information (A-scan information) to segment retinal blood vessels automatically. The technique described here is independent of and does not rely on retinal segmentation methodology, which often fails under the impact of retinal pathologies.

More specifically, the present invention contemplates an automated retinal blood vessel segmentation technique that is based on 3D SD-OCT and that provides accurate vessel pattern for clinical analysis, retinal image registration, early diagnosis and monitoring of the progression of glaucoma and other retinal diseases. The technique of the invention uses a machine learning algorithm to identify blood vessel automatically on 3D OCT image, in a manner that does not rely on and can exclude any other processing. The technique can comprise two components, (i) training the algorithm and (ii) executing the trained algorithm. In one embodiment, the technique can comprise seven steps:

1. Select several 3D OCT images with clear appearance of blood vessel as training images. Generate OCT fundus image (2D projection image) by averaging the intensity values of each A-scan.
2. Manually label each A-scan on OCT fundus image as either vessel or non-vessel.
3. Generate training set by randomly selecting a certain number of vessel A-scans and a certain number of non-vessel A-scans.
4. Generate features for each A-scan: Extract 2D features from the OCT fundus image by taking the responses of $0^{th}$-to-$2^{nd}$ order derivative Gaussian filters. Extract the third dimensional features by applying Haar-function filters on A-scan and taking filter responses.
5. Train the ensemble classifier using boosting learning algorithm. The ensemble classifier is the weighted summation of certain number of base classifiers.
6. Segment blood vessel of the given 3D OCT image using trained classifier. Classify each A-scan to either vessel or non-vessel and generate a binary vessel image.
7. Post-process the binary vessel image to remove the false classification and to smooth the line representing the vessel in the binary vessel image.

One embodiment provides a method of training an algorithm to identify automatically a blood vessel in a three-dimensional optical coherence tomography image, the method comprising: (A) obtaining at least one fundus image generated from A-scans of a plurality of three-dimensional optical coherence tomographic images containing said vessel; (B) labeling each pixel in said fundus image as vessel containing or non vessel containing; (C) generating at least one training data set by selecting randomly from said plurality a first number of said A-scans corresponding to said respective vessel containing pixels and a second number of said A-scans corresponding to said respective non vessel containing pixels; (D) for each A-scan in said training data set, extracting features comprising at least one two-dimensional feature and at least one one-dimensional feature; (E) generating an ensemble classifier by iteratively comparing said features with said corresponding labeled pixels, such that said ensemble classifier is trained to identify automatically said vessel.

In an alternative embodiment, a method of identifying automatically a vessel in a three-dimensional optical coherence tomography image is provided, the method comprising: (A) providing said image; (B) for each A-scan in said image, extracting features comprising at least one two-dimensional feature and at least one one-dimensional feature; (C) generating a binary vessel image by identifying automatically said vessel in said image using an algorithm. The algorithm can be one that has been trained by the method described above.

The methods described above can be a part of a program. For example, the program can be one to train an untrained algorithm. Alternatively, the program can be one that comprises an algorithm already trained by the method described herein to identify automatically a blood vessel in a 3D OCT image. The program, can be recorded on a computer-readable recording medium, such as a diskette, a CD, a DVD, or a hard drive, a portable hard drive. The program can be one that makes an information processing apparatus execute the methods (e.g., in the form of an algorithm) described above. The apparatus can be, for example, a computer. The program and/or the apparatus can be a part of an imaging instrument, such as an optical tomography imaging instrument.

DETAILED DESCRIPTION OF THE PREFERRED EMBODIMENTS

Figure 1A:
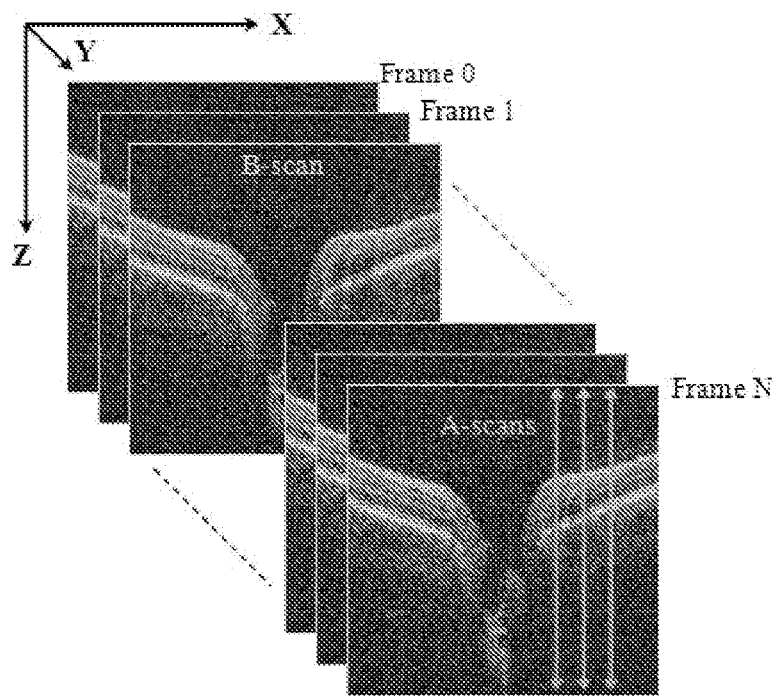
FIG. 1 depicts aspects of a 3D OCT image, including (a) a 3D cube image, constituted from consecutive B-scans, (b) a B-scan, and (c) an OCT fundus image, which averages an entire A-scan.
Figure 1B:
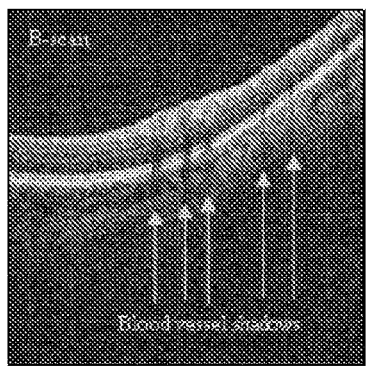
Figure 1C:
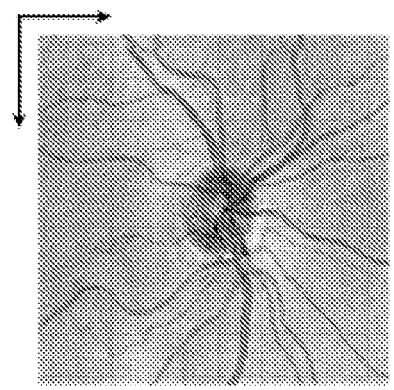
Figure 2:
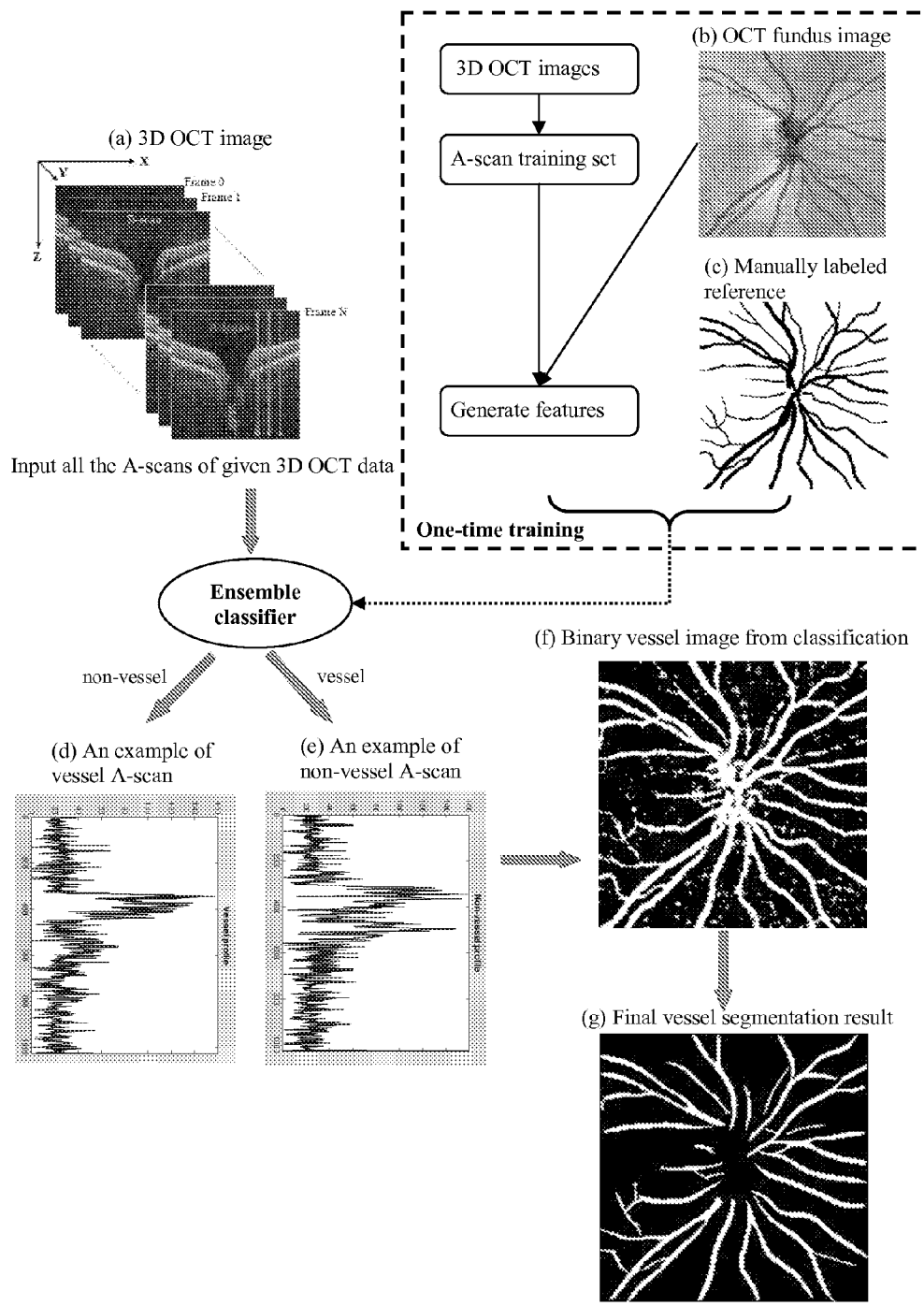
FIG. 2 is a graphic illustration of a machine learning algorithm for blood vessel segmentation pursuant to the invention.

SD-OCT is a new high resolution imaging technique, capable of achieving micrometer resolution in depth. It allows detailed imaging of the eye structures. Currently there is no independent method of retinal blood vessel segmentation on SD-OCT. The present invention provides an automated method to identify blood vessel on 3D OCT image without relying on any processing such as retinal layer segmentation.

The present invention has substantial commercial potential in various applications. It can be used clinically by eye care professionals and also for research purposes. Automated 3D OCT vessel segmentation can be used to measure the abnormal changes of vessel pattern, diameter, width, etc. Moreover it is the fundamental step of retinal image registration with different visits and/or different devices, which has high impact on accurately monitoring eye disease progression so as to have early detection and diagnosis. SD-OCT is currently manufactured by different companies that might be interested to incorporate this method in their product.

As noted above, retinal images take an important role in diagnosis of glaucoma and other retinal diseases. Glaucoma is a group of diseases of the eye characterized by progressive damage of the optic nerve that may result in visual field loss and eventual irreversible blindness if inadequately controlled. The World Health Organization currently ranks glaucoma as the second most common cause of blindness. As the majority of patients do not experience any symptoms until the disease reaches an advanced stage, early detection and treatment is of utmost importance.

Existing ophthalmic imaging techniques for wide range retina imaging are retinal photography, scanning laser ophthalmoscope (SLO), and optical coherence tomography (OCT). Spectral domain optical coherence tomography (SD-OCT) is a new high resolution imaging technique, capable of achieving micrometer resolution in depth. It allows detailed imaging of the eye structures. The introduction of 3D OCT, by which one can obtain a 3D image (cube image) of the retina, offers a promising means for automated analysis, early detection and monitoring the progression of eye diseases, such as glaucoma, diabetic retinopathy, and others.

3D OCT imaging offers the three-dimensional information (z direction). As noted, the present invention exploits a 3D boosting learning technique to segment retinal blood vessels automatically, using both 2D information on OCT fundus image and the third-dimensional, A-scan information.

In this invention, therefore, an independent and automated retinal blood vessel segmentation technique is provided, with the aim to provide accurate vessel pattern for clinical analysis and retinal image registration. Thus, the 3D OCT vessel segmentation technique of the invention is A-scan classification algorithm including two parts, training and testing. A 3D cube image, taken from SD-OCT, and a corresponding, manually labeled vessel reference are required for training. When one-time training is effected, the algorithm can identify a blood vessel on 3D OCT image automatically, without any user input.

FIG. 2(a)-2(g) presents an overview of the process flow according to the invention. The overall process can be characterized as having two components: (i) training an algorithm to be able to identify automatically blood vessels in a 3D OCT image; (ii) applying and executing a trained algorithm for automated vessel identification/classification. The two components can be used separately or in combination. For example, because the algorithm needs to be trained only once, the algorithm can be trained before the software program containing the algorithm is provided to a commercial user via sales of software installation into the imaging instrument on site. In one embodiment, as illustrated in FIGS. 2(a)-2(g), the steps involved are as follows:

1. Obtaining a Fundus Image from a Series of 3D OCT Image

A 2D OCT fundus image (i.e., a 2D projection image) can be generated by averaging the intensity values of each A-scan line in a series of 3D OCT training images taken with SD-OCT [11]. The 3D OCT images preferably are of good quality, with clear appearance (good, high contrast), of the blood vessels contained therein. It is generally known in the art that in OCT imaging an A-scan refers to an axial depth scan, a B-scan refers to a cross-sectional scan, and a C-scan refers to an enface imaging at an certain depth. As noted above, OCT can be used to scan a portion of an eye, such as the optic nerve head containing the blood vessels.

2. Label Each A-Scan on the Fundus Image as Either Vessel or Non-Vessel.

Each pixel in the fundus image is labeled as vessel containing or non vessel containing. For example, in one embodiment, each pixel is manually labeled via a binary code: positive (vessel) or negative (non-vessel). The manual labeling can be carried out by, for example, manually tracing each of the blood vessels in the fundus image with a drawing software and labeling each pixel containing a trace as positive (or vessel) and a blank or without a trace as negative (non vessel). It is noted that each pixel in the OCT fundus image corresponds to an A-scan in the 3D OCT image data (a "3D cube data").

3. Generate Training Set.

A training data set comprising a predefined number of vessels containing A-scans and a predefined number of non vessel containing A-scans can then be randomly selected from the training 3D OCT images. In one embodiment, the training set is selected from the 3D cube data based on the correspondence between the labeled pixels (from the fundus image) and the A-scans in the cube data. The two predefined numbers can be the same or different.

4. Generate Features for Each A-Scan.

For each A-scan, features can be extracted from the fundus image and the A-scan. For example, the features can comprise at least one two-dimensional feature and at least one one-dimensional feature. The one-dimensional feature can be one-dimensional feature in the third dimension. For example, if the two-dimensional feature is extracted from the x and y direction, the one (and third) dimensional feature can be extracted from the z direction. Specifically, (a) 2D features are extracted on OCT fundus image, denoted by I, by taking the responses of $0^{th}$ to $2^{nd}$ order derivative Gaussian filters (i.e., G, $G_x$, Gy, Gxx, Gyy, Gxy) with various sigma (i.e., s=1, 2, 4, 8, 16 pixels) [1]. The image gradient magnitude and divergence can also be used in combination with the Gaussian filters. As a result, in addition to the intensity of the pixel, 2D features can also include image gradient magnitude (i.e. $\sqrt{I_x^2+I_y^2}$) and divergence ($I_{xx}+I_{yy}$), or combinations thereof.

Figure 3A:
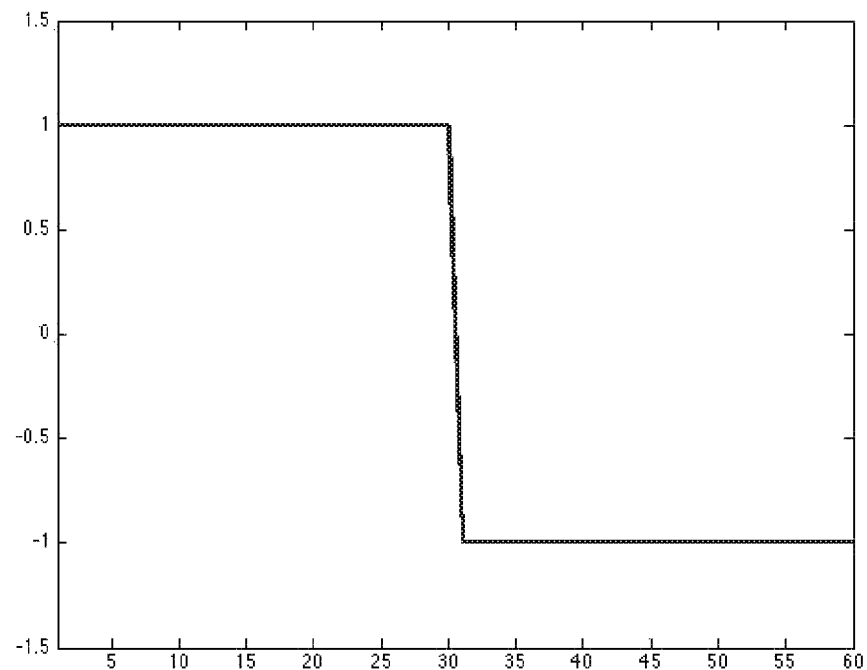
FIG. 3 presents a 1D Haar-feature filter template, with (a) 2-window and (b) 3-window Haar-features.
Figure 3B:
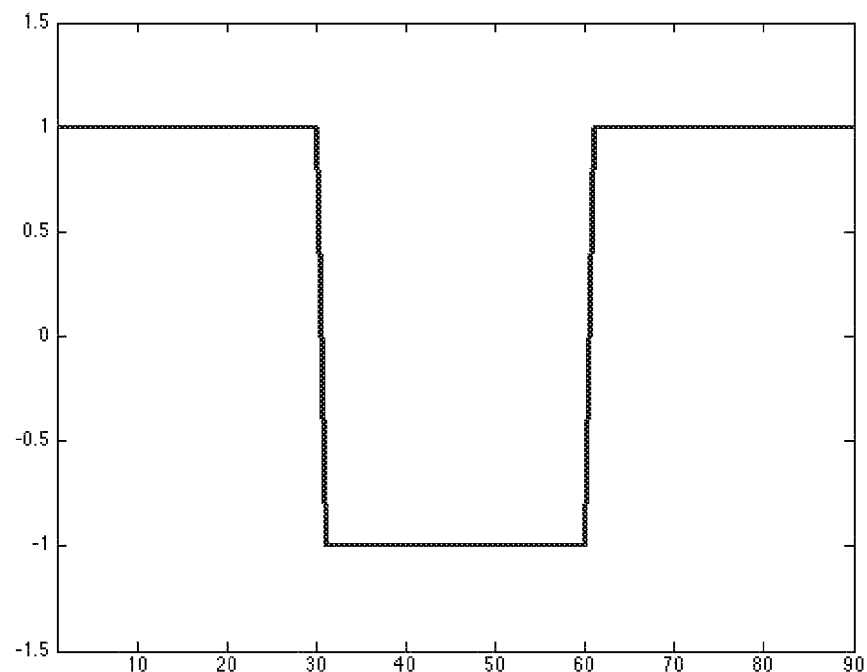

(b) Haar-function filters (1D) with different window sizes can be applied to each A-scan to generate 1D feature from the third dimension. Two kinds of 1D Haar-features can be employed, as shown in FIG. 3(a)-3(b), where −1 and 1 regions have the same window size. The features taken are max, min, max−min, and the $0^{th}$ to $4^{th}$ moments of Haar-function filter responses.

5. Train the Ensemble Classifier Using Boosting-Learning Algorithm.

Figure 4:
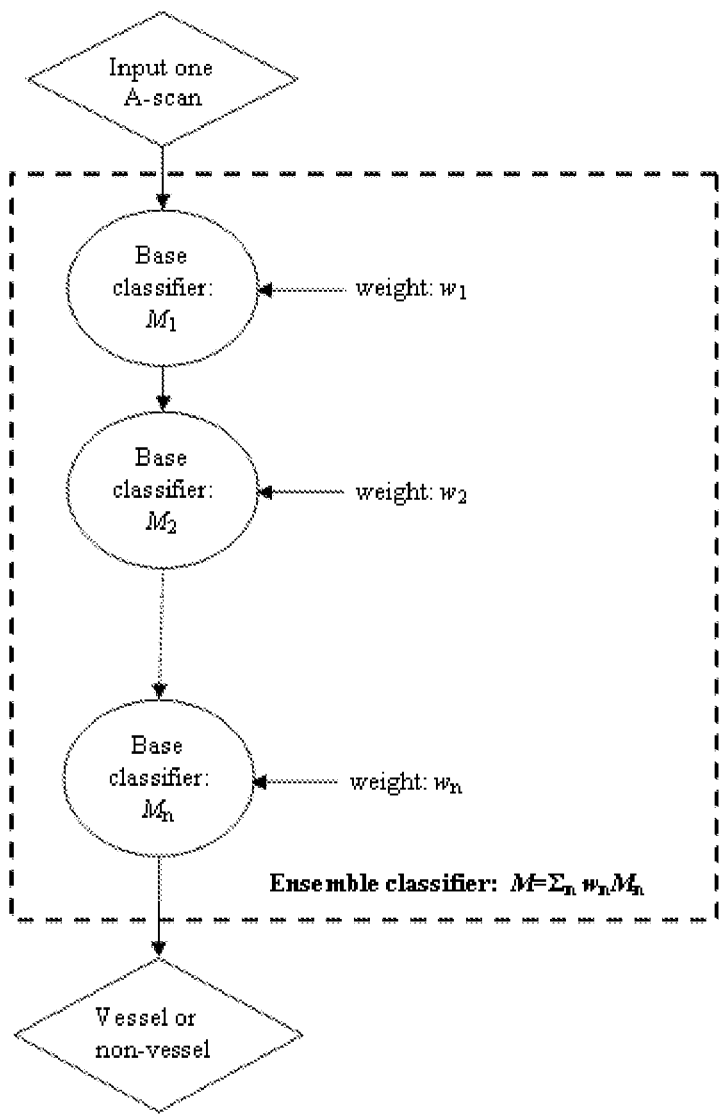
FIG. 4 is a graphic representation of an ensemble classifier, which is the weighted summation of a certain number of base classifiers.

Once a training data set is established, the next step can be to create an algorithm (e.g., a classifier, such as an ensemble classifier) and train it to be able to classify whether an A-scan contains a blood vessel. The training can be carried out by iteratively comparing the training data set with the extracted features and continuously minimizing occurrence of false identification. In one embodiment, the A-scan classification is performed by an implementation of LogitBoost [9] adaptive boosting learning algorithm. The ensemble classifier is trained using shallow depth decision trees as the base classifiers, and it can be in effect the weighted summation of certain number of base classifiers (see FIG. 4). At each boosting round, a sampling distribution over the training data (i.e., manually labeled data) is computed, focusing the training of the current base classifier on samples that are misclassified in the previous round. The base classifier at each round is trained, updated, and added to the ensemble. Subsequent base classifiers are added one by one and the weights are adjusted with each addition, with an objective of minimizing the overall training error (e.g., false classification).

Once an algorithm is trained by the foregoing method, the algorithm can be applied to a new 3D OCT image to identify automatically which A-scan contains a blood vessel. As described before, the algorithm needs to be trained only once. Thus, a software that contains a program containing the algorithm described above can be pre-trained in a laboratory or in the factory before being installed or shipped to an end user or consumer.

At an end user's site, a pre-trained algorithm can then be applied and executed to identify automatically the blood vessel in any 3D OCT image.

6. Segment Blood Vessel of the Given 3D OCT Image.

Figure 5A:
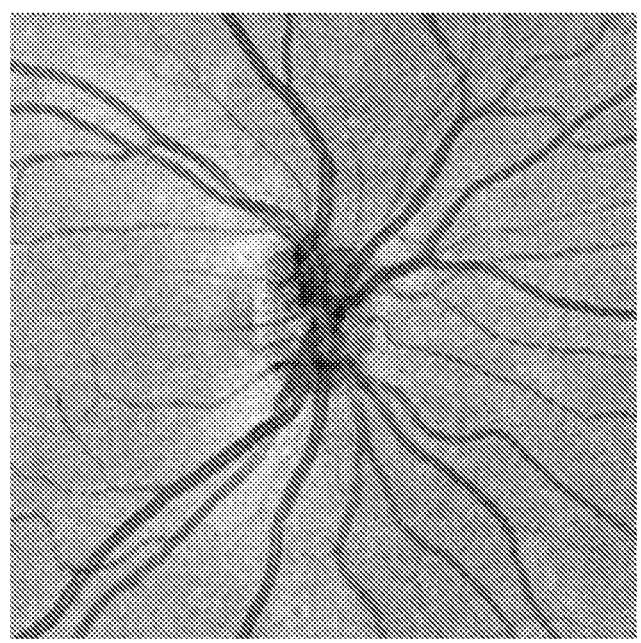
FIG. 5 provides an example of results from a boosting learning vessel segmentation and post-processing in accordance with the invention.
Figure 5B:
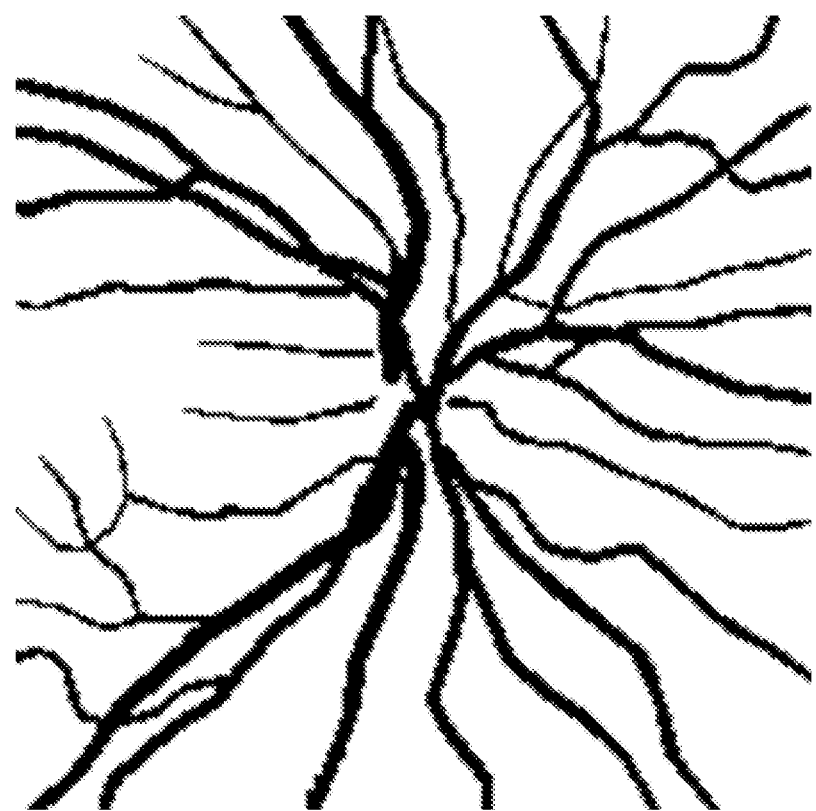
Figure 5C:
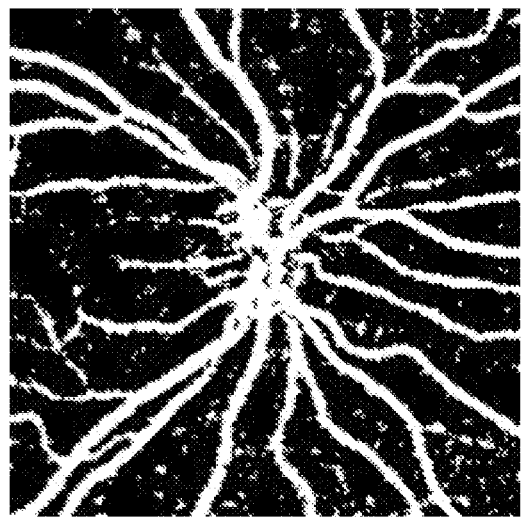
Figure 5D:
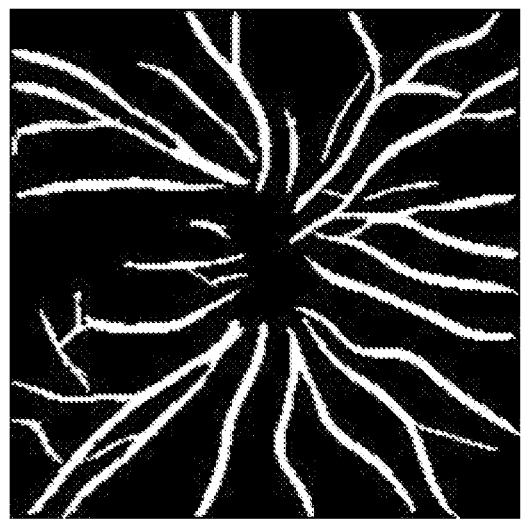

The trained classifier can be applied to new 3D OCT data one A-scan at a time classifying/labeling each A-scan as vessel or non-vessel. In one embodiment, the trained classifier can automatically extract the features (i.e., 2D and/or 1D) from each A-scan of the new 3D OCT image and compare the features with the data set already established from prior training. Upon finishing the classification, the trained classifier can generate a binary vessel image, mapping out what the classifier determines as the blood vessels in the 3D OCT image. See FIG. 5(c).

7. Post-Processing of the Binary Vessel Image

Figure 6:
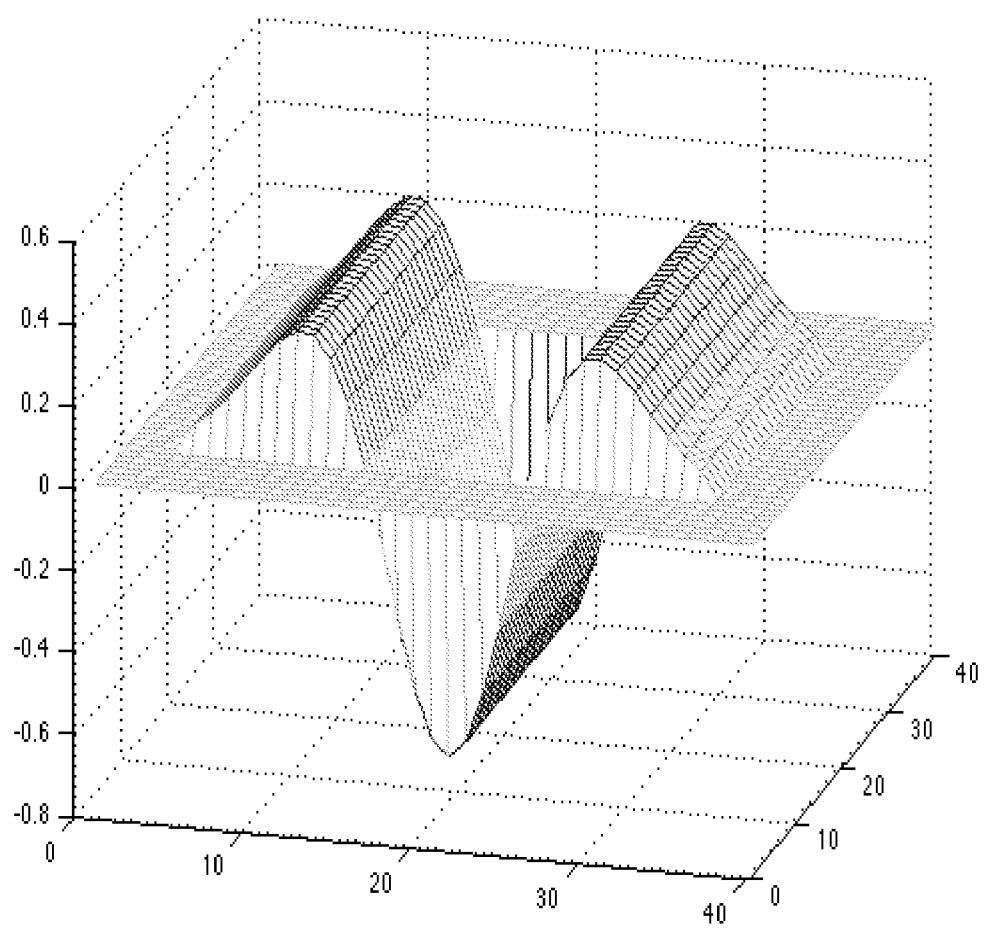
FIG. 6 is a graphic depiction of a normalized 2D second-order Gaussian filter template.

The raw binary vessel image can be further processed to further remove false classifications and/or to further smooth the lines representing the blood vessels in the binary image. In one embodiment, (a) a matched filter algorithm is applied to remove false classifications and smooth the vessel image. A normalized 2D second-order Gaussian filter template (FIG. 6) is used to approximately represent the pattern along the direction of vessel length. The filters with different widths and directions can be applied to the binary vessel image that is obtained from boosting learning. The maximal filter response is taken pixel by pixel.

(b) Additionally, a thresholding operation can be further applied to obtain a binary vessel segmentation result. Optic nerve head (ONH) is segmented using the previously published method [10] and masked on the maximal filter response image to reduce the negative effect of thresholding operation.

The invention offers several advantages over conventional technology. The above-described technique is an independent method and does not rely on any other processing, such as retinal layer segmentation, which often fails in the presence of retinal pathologies or in the region with optic disc. Moreover, the invention makes use of both 2D information and 3D information (arising from the third dimensional feature) to detect the blood vessel, which makes the method robust, with minimal noise.

NON-LIMITING WORKING EXAMPLES

The present invention is further illustrated by reference to the following description of methodology within the invention and corresponding results. See [12].

Methodology

A supervised pixel (A-scan projection on 2D OCT fundus image) classification algorithm is proposed to automatically segment blood vessels on 3D OCT image. 2D derivative Gaussian filters, divergence, gradient magnitude and the third dimensional Haar-function filters are used to generate feature space. Boosting learning is applied to train the classifier and segment the image A-scan by A-scan. The binary vessel image is smoothed by matched filter for post-processing

Feature Extraction

OCT fundus image, donated by I, is generated by averaging each A-scan. 2D features are extracted on OCT fundus image by taking the responses of $0^{th}$ to $2^{nd}$ order derivative Gaussian filters (i.e., G, $G_x$, $G_y$, $G_{xx}$; $G_{yy}$, $G_{xy}$) with various sigma (i.e., $\sigma$ =1, 2, 4, 8, 16 pixels) [1]. Image gradient magnitude (i.e., $\sqrt{I_x^2+I_y^2}$) and divergence ($I_{xx}+I_{yy}$) also are included in the 2D feature extraction process and the values thereof can be a part of the 2D features.

One-dimensional Haar-function filters with different window sizes are applied on each A-scan to generate the third dimensional features. By way of illustration, two kinds of 1D Haar-features were applied as shown in FIG. 3, where −1 and 1 regions have the same window size. The features taken are max, min, max-min, and $0^{th}$ to $4^{th}$ moments of Haar-function filter responses.

Boosting Learning

The A-scan classification was performed by an implementation of LogitBoost [9] adaptive boosting algorithm. The ensemble classifier was trained using shallow depth decision trees as the base classifiers. At each boosting round a sampling distribution over the training data is computed that focuses the training of the current base classifier on samples that were misclassified in the previous round. The base classifier was trained and added to the ensemble. Subsequent base classifiers were added one by one and the weights are adjusted with each addition, with the goal of minimizing the overall training error. Training was conducted by hand labeling a collection of A-scans as positive (vessel) and negative (non-vessel) examples. The classifier was applied to new testing data one A-scan at a time labeling each sample as vessel or non-vessel.

Post Processing

A matched filter algorithm is applied to remove false classifications and smooth the vessel image. A normalized 2D second-order Gaussian filter template (FIG. 6) was used to approximately represent the pattern along the direction of vessel length. The template, modified based on Eq. (10) in [3], is written as formula (1):

$$G(x, y) = kR(\theta)h(x, y) = kR(\theta)\frac{1}{\sqrt{2\pi\sigma^2}}(x^2 - \sigma^2)e^{-\left(\frac{x^2}{2\sigma^2}\right)} \quad (1)$$

$$y \leq L, |x - x_0| \leq W/2,$$

$$k = \sum_{xy} R(\theta)h(x, y)$$

where L (the vessel direction) and W are the length and width of filter template respectively, a corresponds to vessel width, $x_0$ is the center location along the vessel direction, k is the normalized coefficient, and R is the rotation matrix according to vessel orientation. Directional filters are generated using the rotation matrix R with the rotation angle θ. The filters with different σ and θ are employed on the binary vessel image that is obtained from the boosting-learning process. The maximal filter response is taken pixel by pixel, and a thresholding operation is applied to obtain a final vessel-segmentation result.

The optic nerve head (ONH) is segmented, via a published method [10], and masked to reduce the negative effect of thresholding operation.

Evaluation

The A-scan classification outcome can be positive (vessel) and negative (non-vessel). Sensitivity and specificity are used to evaluate the classification result per A-scan.

Results

Twelve 3D OCT images centered at ONH, taken from healthy subjects, were acquired using SD-OCT effect with Cirrus HDOCT, product of Carl Zeiss Meditec, Inc. (Dublin, Calif.). The image resolution is 200×200×1024 samplings in a cube of 6×6×2 mm. One image with the best quality was set to be the training image and the other 11 were in the testing set. Each image has 200×200 A-scans, which were manually labeled as either vessel or non-vessel the on OCT fundus image. Four hundred vessel A-scans and four hundred non-vessel A-scans were randomly selected from training image to generate training set. Two-dimensional features and three-dimensional Haar-features were extracted to train the ensemble classifier. The one-time training took 134 seconds, using MATLAB, and each 3D OCT image took 1000 seconds to segment.

An example of boosting learning vessel segmentation and post-processing results is given in FIG. 5. The manually labeled reference and classification results are shown in FIGS. 5(b) and (c). Matched filter approach efficiently removed the false classifications and smoothed the blood vessels (FIG. 5(d)). Table 1 shows the sensitivity and specificity of each testing image, where positive and negative correspond to vessel and non-vessel respectively. The average sensitivity was 85%, with specificity of 88%.

TABLE 1

Comparison of the result of the vessel segmentation algorithm with the manually marked reference

| Image | Sensitivity | Specificity |
|---|---|---|
| 1 | 0.90 | 0.88 |
| 2 | 0.84 | 0.85 |
| 3 | 0.90 | 0.90 |
| 4 | 0.87 | 0.93 |
| 5 | 0.81 | 0.85 |
| 6 | 0.89 | 0.85 |
| 7 | 0.71 | 0.90 |
| 8 | 0.85 | 0.87 |
| 9 | 0.82 | 0.86 |
| 10 | 0.90 | 0.90 |
| 11 | 0.89 | 0.86 |
| Mean | 0.85 | 0.88 |

The main difficulty of OCT image vessel segmentation is the weak visibility of vessel pattern on the OCT fundus image. The 3D boosting learning approach of this invention allows for automated segmentation of retinal blood vessels, using the three-dimensional information. The inventive algorithm does not rely on retinal layer segmentation. The foregoing experimental results show that the algorithm is an efficient way to segment the blood vessel on 3D OCT image.

All references, including publications, patents, and patent applications, that are cited in this description are hereby incorporated by reference in their entirety.

While specific embodiments of the subject invention have been discussed, the above Specification is illustrative and not restrictive. Many variations of the invention will become apparent to those skilled in the art upon review of this specification. The full scope of the invention should be determined by reference to the claims, along with their full scope of equivalents, and the specification, along with such variations.

The articles "a" and "an" are used herein to refer to one or to more than one (i.e. to at least one) of the grammatical object of the article. By way of example, "a polymer resin" means one polymer resin or more than one polymer resin. Any ranges cited herein are inclusive. The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

REFERENCES

[1] M. Niemeijer, M. K. Garvin, B. Ginneken, M. Sonka, M. D. Abramoff, "Vessel segmentation in 3D spectral OCT scans of the retina," *Proc. SPIE Conf. on Medical Imaging*, vol. 6914, pp. 69141R1-69141R8, 2008.

[2] S. Chaudhuri, S. Chatterjee, N. Katz, M. Nelson, and M. Goldbaum, "Detection of blood vessels in retinal images using two-dimensional matched filters," *IEEE Transactions on Medical Imaging*, vol. 8, no. 3, pp. 263-269, September 1989.

[3] L. Gang, O. Chutatape, S. M. Krishnan, "Detection and measurement of retinal vessels in fundus images using amplitude modified second-order Gaussian filter," *IEEE Transactions on Biomedical Engineering*, vol. 49, No. 2, pp. 168-172, February 2002.

[4] A. Hoover, V. Kouznetsova, and M. Goldbaum, "Locating blood vessels in retinal images by piecewise threshold probing of a matched filter response," *IEEE Transactions on Medical Imaging*, vol. 19, no. 3, pp. 203-210, 2000.

[5] A. Can, H. Shen, J. N. Turner, H. L. Tanenbaum, B. Roysam, "Rapid Automated Tracing and Feature Extraction from Retinal Fundus Images Using Direct Exploratory Algorithms," *IEEE Transactions on Information Technology in Biomedicine*, vol. 3, no. 2, pp. 125-138, June 1999.

[6] F. Zana and J. Klein, "Segmentation of vessel-like patterns using mathematical morphology and curvature evaluation," *IEEE Transactions on Image Processing*, vol. 10, no. 7, pp. 1010-1019, 2001.

[7] J. J. Staal, M. D. Abramoff, M. Niemeijer, M. A. Viergever, B. van Ginneken, "Ridge based vessel segmentation in color images of the retina," *IEEE Transactions on Medical Imaging*, vol. 23, pp. 501-509, 2004.

[8] C. Sinthanayothin, J. F. Boyce, H. L. Cook, and T. H. Williamson, "Automated localization of the optic disc, fovea and retinal blood vessels from digital color fundus images," *Br. J. Ophthalmol.*, vol. 83, pp. 231-238, August 1999.

[9] Jerome Friedman, Trevor Hastie and Robert Tibshirani. Additive logistic regression: a statistical view of boosting. *Annals of Statistics* 28(2), 2000.337-407

[10] J. Xu, O. Chutatape, P. Chew, "Automated optic disk boundary detection by modified active contour model," *IEEE Trans. on Biomedical Engineering*, vol. 54, no. 3, March 2007.

[11] Knighton, Robert W, Jiao, Shuliang, Gregori, Giovanni and Puliafito, Carmen A, "Enhanced optical coherence tomography for anatomical mapping," US patent 20060119858 (August 2006).

[12] J. Xu, D. A. Tolliver, H. Ishikawa, G. Wollstein, J. S. Schuman, "3D OCT retinal vessel segmentation based on boosting learning", in *IFMBE Proceedings of World Congress on Medical Physics and Biomedical Engineering (WC2009)*, vol. 25/11, pp. 179-182, September 2009.

What is claimed:

1. A method of training an algorithm to identify automatically a blood vessel in a three-dimensional optical coherence tomography image, comprising:
   (A) obtaining at least one fundus image generated from A-scans of a plurality of three-dimensional optical coherence tomographic images containing said vessel;
   (B) labeling each pixel in said fundus image as vessel containing or non vessel containing;
   (C) generating at least one training data set by selecting randomly from said plurality a first number of said A-scans corresponding to said respective vessel containing pixels and a second number of said A-scans corresponding to said respective non vessel containing pixels;
   (D) for each A-scan in said training data set, extracting features comprising at least one two-dimensional feature and at least one one-dimensional feature;
   (E) generating an ensemble classifier by iteratively comparing said features with said corresponding labeled pixels, such that said ensemble classifier is trained to identify automatically said vessel.

2. The method of claim 1, wherein step (B) is carried out manually.

3. The method of claim 1, wherein said two-dimensional feature is extracted with 0th to 2nd order derivative Gaussian filters, gradient magnitude, and divergence.

4. The method of claim 1, wherein said one-dimensional feature is extracted with Haar-function filters.

5. The method of claim 1, wherein step (E) is carried out with a boosting learning algorithm.

6. A non-transitory computer-readable recording medium, recorded thereon a program comprising an algorithm trained by the method of claim 1.

7. An imaging instrument configured to execute the program stored on the non-transitory computer-readable recording medium of claim 6.

8. A method of identifying automatically a vessel in a three-dimensional optical coherence tomography image, comprising:
   (A) providing said image;
   (B) for each A-scan in said image, extracting features comprising at least one two-dimensional feature and at least one one-dimensional feature;
   (C) generating a binary vessel image by identifying automatically said vessel in said image using an algorithm.

9. The method of claim 8, wherein said algorithm is trained by a method comprising:
   (A) obtaining at least one fundus image generated from A-scans of a plurality of three-dimensional optical coherence tomographic images containing said vessel;
   (B) labeling each pixel in said fundus image as vessel containing or non vessel containing;
   (C) generating at least one training data set by selecting randomly from said plurality a first number of said A-scans corresponding to said respective vessel containing pixels and a second number of said A-scans corresponding to said respective non vessel containing pixels;
   (D) for each A-scan in said training data set, extracting features comprising at least one two-dimensional feature and at least one one-dimensional feature;
   (E) generating an ensemble classifier by iteratively comparing said features with said corresponding labeled pixels, such that said ensemble classifier is trained to identify automatically said vessel.

10. The method of claim 8, further comprising at least one of (i) removing false classification and (ii) smoothing said vessel in said binary vessel image.

11. A non-transitory computer-readable recording medium, recorded thereon a program that makes an information processing apparatus execute the method of claim 8.

12. The non-transitory computer-readable recording medium of claim 11, wherein the information process apparatus is a part of an imaging instrument.

* * * * *